(12) United States Patent
Greenberg et al.

(10) Patent No.: US 8,014,868 B2
(45) Date of Patent: *Sep. 6, 2011

(54) ELECTRODE ARRAY FOR EVEN NEURAL PRESSURE

(75) Inventors: Robert J. Greenberg, Los Angeles, CA (US); Mark S. Humayun, Glendale, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 104 days.

This patent is subject to a terminal disclaimer.

(21) Appl. No.: 12/258,296

(22) Filed: Oct. 24, 2008

(65) Prior Publication Data

US 2009/0149915 A1    Jun. 11, 2009

Related U.S. Application Data

(60) Provisional application No. 60/982,357, filed on Oct. 24, 2007.

(51) Int. Cl.
*A61N 1/00* (2006.01)

(52) U.S. Cl. ............................................. 607/53

(58) Field of Classification Search ............ 607/54
See application file for complete search history.

(56) References Cited

U.S. PATENT DOCUMENTS

| 5,109,844 | A | 5/1992 | de Juan, Jr. et al. |
| 5,575,813 | A | 11/1996 | Edell et al. |
| 5,935,155 | A * | 8/1999 | Humayun et al. ............ 607/54 |
| 6,400,989 | B1 | 6/2002 | Eckmiller |
| 6,458,157 | B1 | 10/2002 | Suaning |
| 6,564,079 | B1 * | 5/2003 | Cory et al. .................... 600/393 |
| 2003/0069603 | A1 * | 4/2003 | Little et al. ................... 606/219 |
| 2006/0173511 | A1 * | 8/2006 | Greenberg et al. ............ 607/54 |
| 2007/0055336 | A1 | 3/2007 | Greenberg |
| 2009/0228086 | A1 * | 9/2009 | Greenberg et al. ........... 607/116 |

* cited by examiner

*Primary Examiner* — George Manuel
*Assistant Examiner* — Robert N Wieland
(74) *Attorney, Agent, or Firm* — Scott B. Dunbar

(57) ABSTRACT

The present invention is an electrode array for neural stimulation. In particular it is an electrode array for use with a visual prosthesis with the electrode array suitable to be positioned on the retina. The array includes multiple attachment points to provide for even pressure across the electrode array surface. The attachment points are arranged so as to not damage retinal tissue stimulated by the electrode array.

17 Claims, 6 Drawing Sheets

ELECTRODE ARRAY FOR EVEN NEURAL PRESSURE

CROSS REFERENCE TO RELATED APPLICATIONS

This application claims benefit of U.S. Provisional Patent Application 60/982,357, filed Oct. 24, 2007, for Electrode Array for Even Retinal Pressure. This application is related to and incorporates by reference, U.S. patent application Ser. No. 12/163,658, filed Jun. 27, 2008, for Flexible Circuit Electrode Array.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved method of improving resolution by selectively stimulating smaller cells.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across retinal neuronal cell membranes, which can initiate retinal neuronal action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the retinal neurons, and avoid undue compression of the retinal neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated a cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Opthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY OF THE INVENTION

The present invention is a visual prosthesis having an electrode array suitable to be positioned on the retina. The array includes multiple attachment points to provide for even pressure across the electrode array surface. The attachment points are arranged so as to not damage retinal tissue stimulated by the electrode array.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
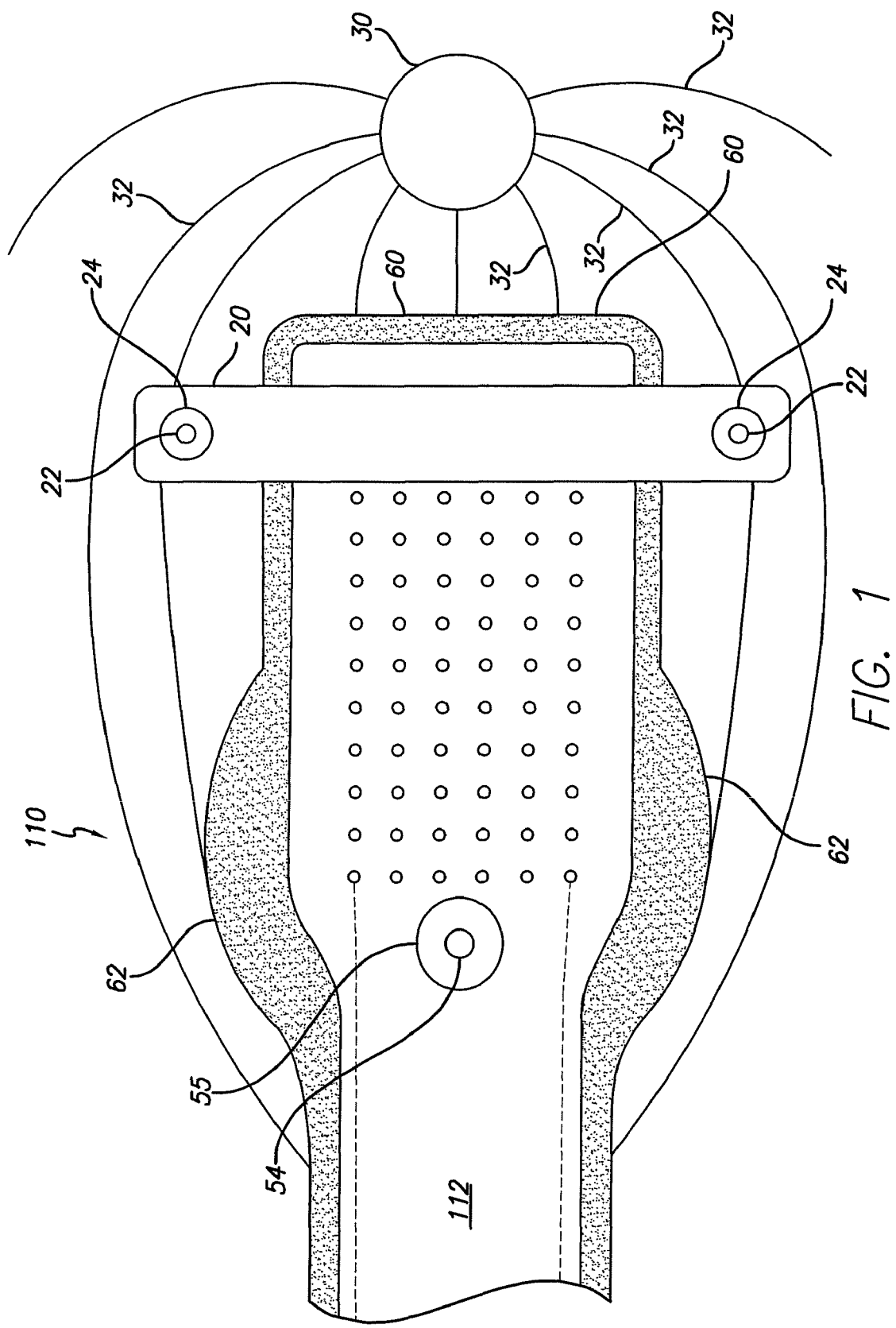
FIG. 1 depicts the electrode array of the preferred embodiment.

FIG. 1 shows the flexible circuit electrode array of the current invention. A flexible circuit cable 112 connects to the flexible circuit electrode array 110. Further, a primary attachment point 54 is provided near the heel of the flexible circuit electrode array 110. A retina tack (not shown) is placed through the primary attachment point 54 to hold the flexible circuit electrode array 110 to the retina or other neural tissue. A stress relief 55 is provided surrounding the attachment point 54. The stress relief 55 may be made of a softer polymer than the flexible circuit, or it may include cutouts or thinning of the polymer to reduce the stress transmitted from the retina tack to the flexible circuit electrode array 110. A skirt or molded body 60 covers the flexible circuit electrode array 10, and extends beyond its edges. It is further advantageous to include wings 62 adjacent to the attachment point 54 to spread any stress of attachment over a larger area of the retina or other neural tissue. There are several ways of forming and bonding the skirt 60. The skirt 60 may be directly bonded through surface activation or indirectly bonded using an adhesive. The skirt 60 may be a molded body from completely around the electrode array 110 and cable 112.

Preferably the electrode array 110 is constructed from a hard polymer such as polyimide while the skirt 60 is constructed from a softer polymer such as silicone. Traces and electrodes can be laid out on a hard polymer by photolithography and the hard polymer protects the delicate traces. A soft polymer skirt or molded body 60 then protects the neural tissue from the hard polymer.

Further a strap 20 may be provided over the array 110 opposite the primary attachment point 54 attached at either end by secondary attachment points 22 with retinal tacks. The secondary attachment points 22 include stress relief 24 like the stress relief 55 described above. Retinal nerve fibers and blood vessels run orbitally out from the optic nerve. It is advantageous not to tack between the electrode array 110 and the optic nerve as you may damage the nerve fibers which are stimulated by the electrode array 110. The strap 20 allows the secondary attachment points 22 to be out of the line of the stimulated nerve fibers. The optic nerve 30 is the central access point for both nerve fibers and blood vessels. 32. A tack through either a nerve fiber or blood vessel may cause damage to the area to be stimulated by the electrode array 110.

Figure 2:
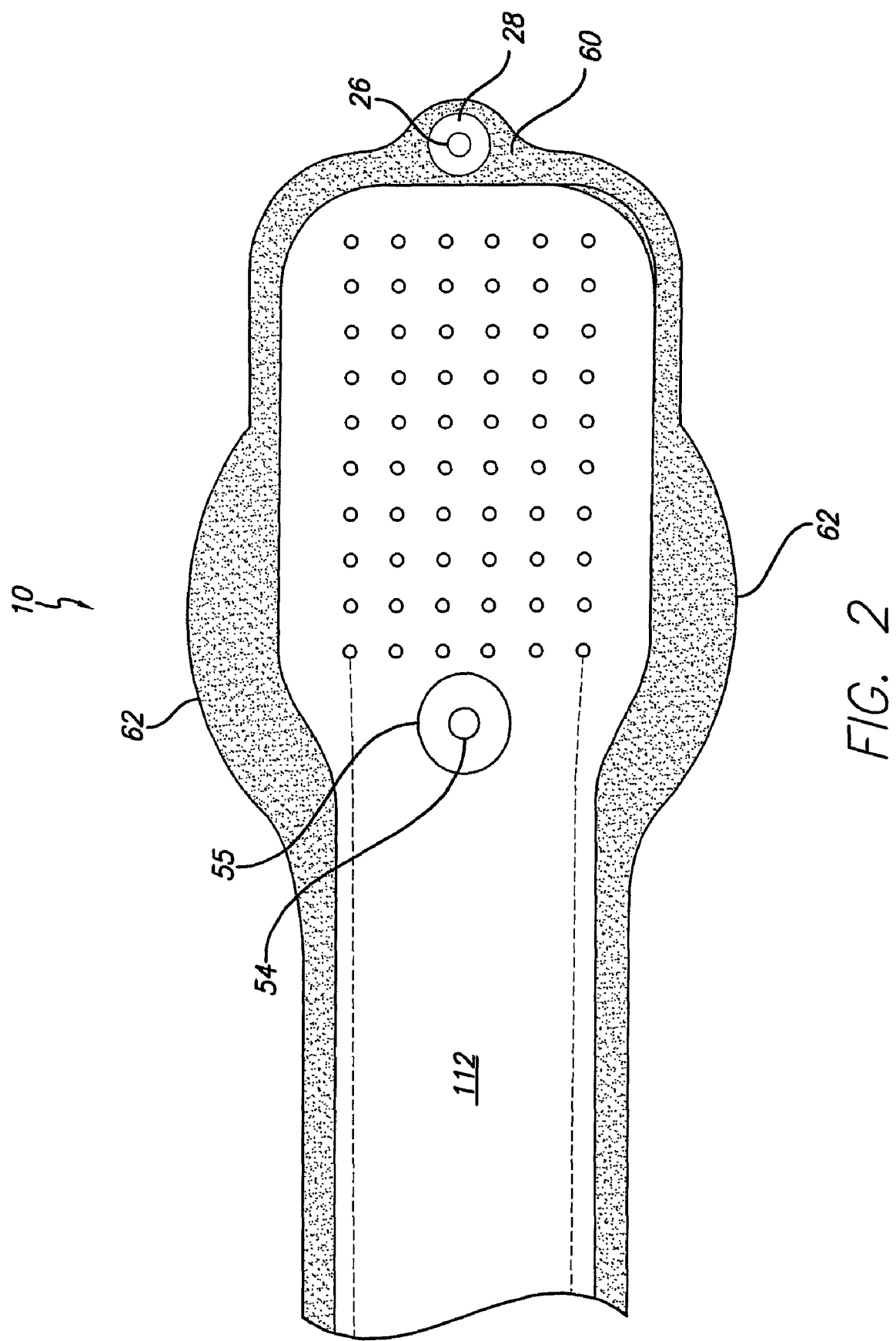
FIG. 2 depicts an electrode array of an alternate two point attachment

Alternatively, FIG. 2 show a central secondary attachment point 26, with a stress relief 28. If the array is not aligned with the nerve fibers a central secondary attachment point may be preferable.

Figure 3:
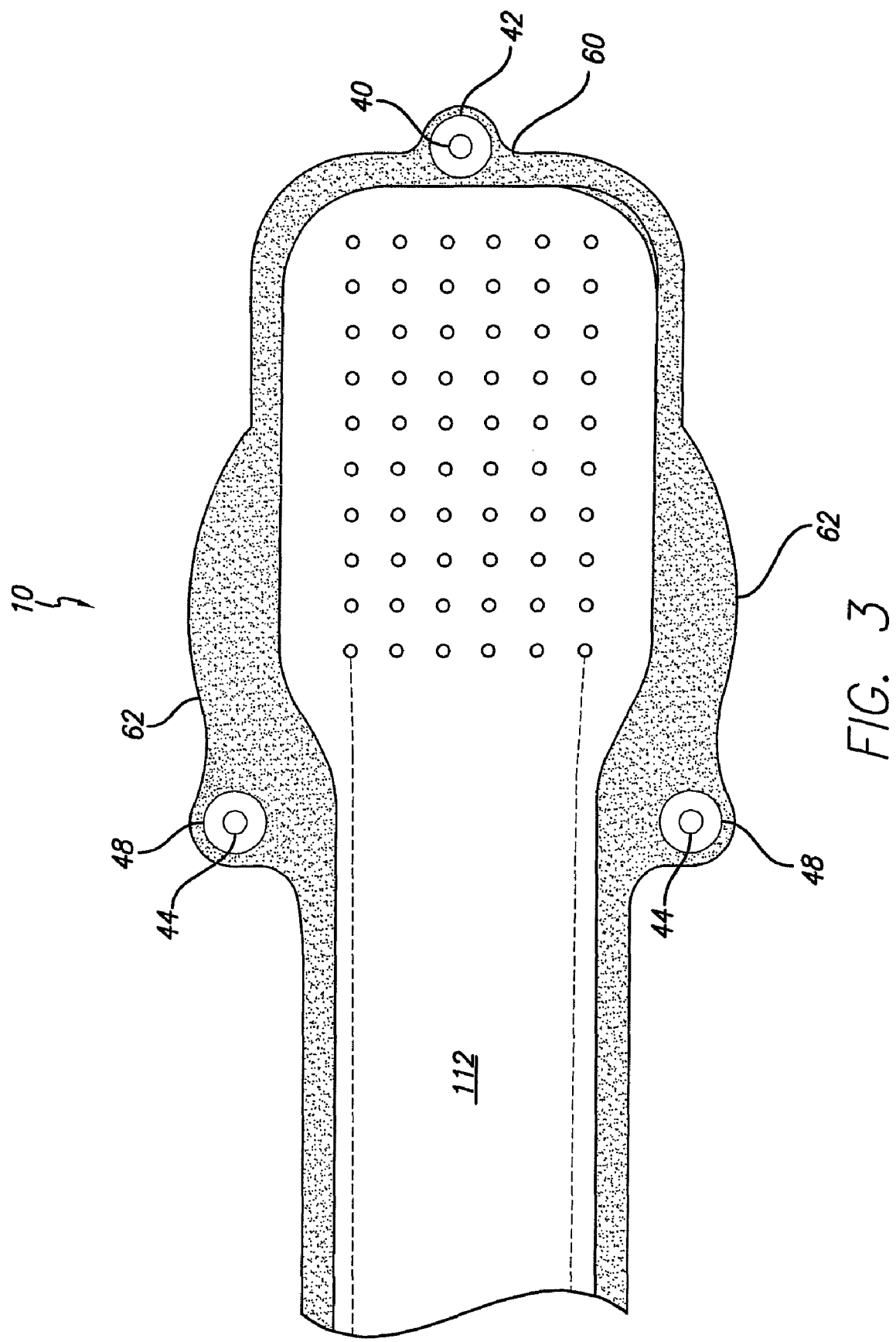
FIG. 3 depicts an electrode array of an alternate three point attachment.

FIG. 3 show a second alternate embodiment. It this case the array may be place in the opposite orientation, with the cable passing over the optic nerve. The primary attachment point 40 includes a stress relief 42. The secondary attachment points 44, with stress relief 48, are included in the wings 62.

Figure 4:
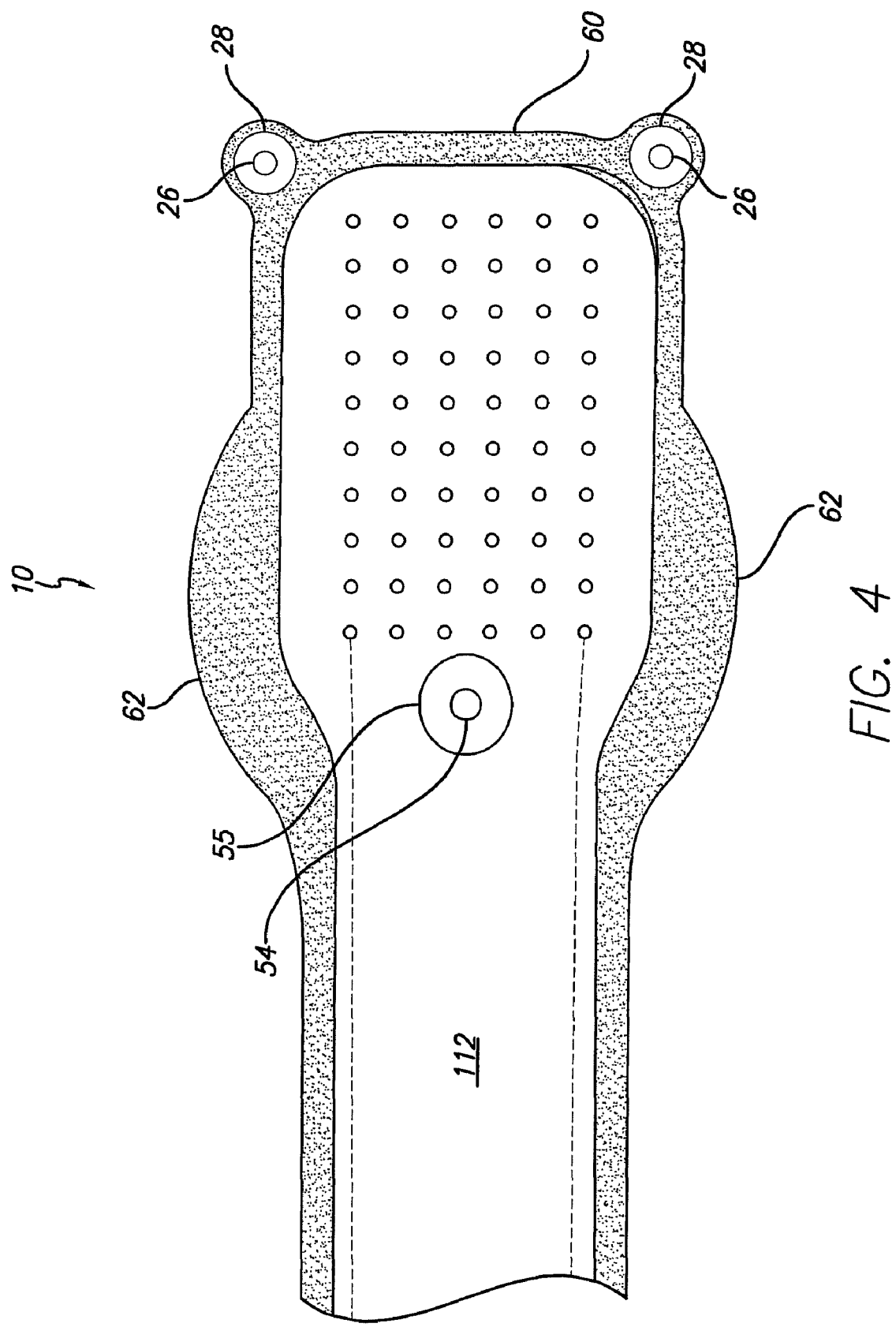
FIG. 4 depicts an electrode array with another alternate three point attachment.

FIG. 4 shows another alternate embodiment similar to the embodiment shown in FIG. 1, but with the secondary attachment points 26 integral to the array body rather than on a separate strap. As with the embodiment of FIG. 1, the secondary attachment points are outside of the area of the nerve fibers and blood vessels supplying the areas to be stimulated.

Figure 5:
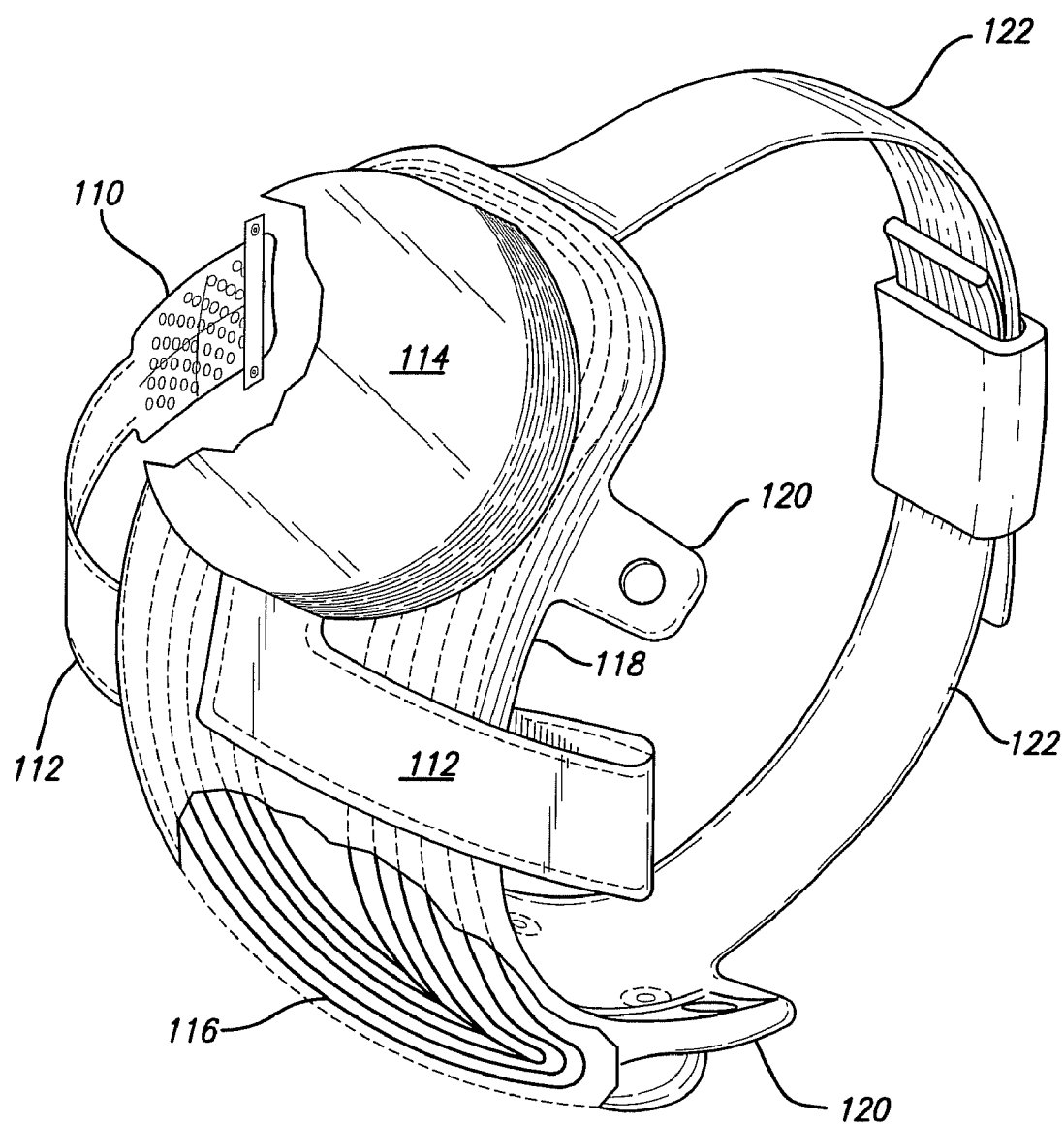
FIG. 5 is a perspective view of the implanted portion of the preferred visual prosthesis.

FIG. 5 shows a perspective view of the implanted portion of the preferred retinal prosthesis. An electrode array 110 is mounted by a retinal tack or similar means to the epiretinal surface. The electrode array 110 is electrically coupled by a cable 112, which pierces the sclera and is electrically coupled to an electronics package 114, external to the sclera.

The electronics package 114 is electrically coupled to a secondary inductive coil 116. Preferably the secondary inductive coil 116 is made from wound wire. Alternatively, the secondary inductive coil may be made from a thin film polymer sandwich with wire traces deposited between layers of thin film polymer. The electronics package 114 and secondary inductive coil 116 are held together by a molded body 118. The molded body 118 may also include suture tabs 120. The molded body narrows to form a strap 122 which surrounds the sclera and holds the molded body 118, secondary inductive coil 116, and electronics package 114 in place. The molded body 118, suture tabs 120 and strap 122 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 116 and molded body 118 are preferably oval shaped. A strap can better support an oval shaped coil.

It should be noted that the entire implant is attached to and supported by the sclera. An eye moves constantly. The eye moves to scan a scene and also has a jitter motion to prevent image stabilization. Even though such motion is useless in the blind, it often continues long after a person has lost their sight. It is an advantage of the present design, that the entire implanted portion of the prosthesis is attached to and supported by the sclera. By placing the device under the rectus muscles with the electronics package in an area of fatty issue between the rectus muscles, eye motion does not cause any flexing which might fatigue, and eventually damage, the device.

Figure 6:
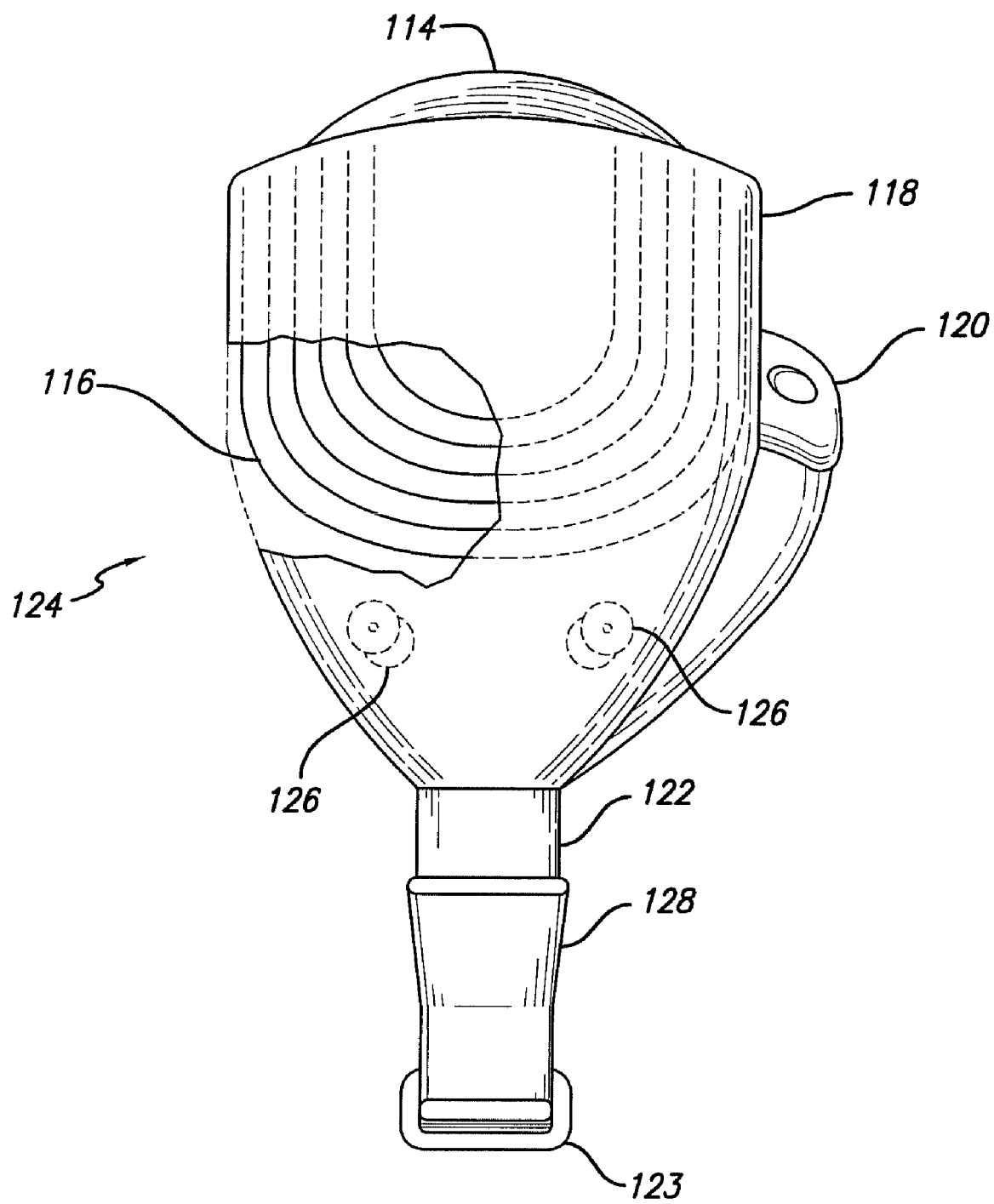
FIG. 6 is a side view of the implanted portion of the preferred visual prosthesis showing the fan tail in more detail.

FIG. 6 shows a side view of the implanted portion of the retinal prosthesis, in particular, emphasizing the fan tail 124. When implanting the retinal prosthesis, it is necessary to pass the strap 122 under the eye muscles to surround the sclera. The secondary inductive coil 116 and molded body 118 must also follow the strap under the lateral rectus muscle on the side of the sclera. The implanted portion of the retinal prosthesis is very delicate. It is easy to tear the molded body 118 or break wires in the secondary inductive coil 116. In order to allow the molded body 118 to slide smoothly under the lateral rectus muscle, the molded body is shaped in the form of a fan tail 124 on the end opposite the electronics package 114.

Accordingly, what has been shown is an improved method of making a neural prosthesis and an improved method of stimulating neural tissue. While the invention has been described by means of specific embodiments and applications thereof, it is understood that numerous modifications and variations could be made thereto by those skilled in the art without departing from the spirit and scope of the invention. In particular, the preferred embodiment describes a retinal prosthesis for artificial vision. It should be obvious to one skilled in the art that the invention has broad applicability to other types of neural stimulation. It is therefore to be understood that within the scope of the claims, the invention may be practiced otherwise than as specifically described herein.

The invention claimed is:

1. An electrode array for neural stimulation comprising:
   an array body comprising an electrode array and a skirt body surrounding said electrode array, said array body comprising a proximate heel portion connected to a supply cable and a distal toe portion along said array body;
   a primary attachment point for attaching said array body to neural tissue disposed within said heel portion, and
   a secondary attachment point for attaching said array body to neural tissue disposed distal to said primary attachment point and positioned within said skirt body in said toe portion.

2. The electrode array according to claim 1, having a plurality of attachment points in said heel.

3. The electrode array according to claim 1, having a plurality of attachment points in said toe.

4. The electrode array according to claim 1, further comprising stress relief portions between said attachment points and said array body.

5. The electrode array according to claim 4, wherein said stress relief portion is a soft polymer.

6. The electrode array according to claim 1, wherein said electrode array is suitable to contact retinal tissue to electrically induce artificial vision.

7. The electrode array according to claim 1, wherein said electrode array body comprises a soft polymer formed over a hard polymer.

8. The electrode array according to claim 7, wherein said attachment points are formed in said soft polymer.

9. The electrode array according to claim 1, where said secondary attachment point is near a center line of a long axis on a opposite side of said array from said primary attachment point.

10. An electrode array for neural stimulation comprising;
    an electrode array for stimulating neural tissue within an array body having a heel proximate to a supply cable and a toe opposite said heel;
    a attachment point within said array body; and
    a strap, separate from said array body having a plurality of attachment points suitable to locate said array body proximate to neural tissue.

11. The electrode array according to claim 10, wherein said attachment point within said array body is within said heel and said strap is suitable to locate said toe.

12. The electrode array according to claim 10, wherein said attachment point within said array body is within said toe and said strap is suitable to locate said heel.

13. The electrode array according to claim 10, further comprising a stress relief between said attachment points and said array body.

14. The electrode array according to claim 13, wherein said stress relief portion is a soft polymer.

15. The electrode array according to claim 10, wherein said electrode array is suitable to contact retinal tissue to electrically induce artificial vision.

16. The electrode array according to claim 10, wherein said electrode array body comprises a soft polymer formed over a hard polymer.

17. The electrode array according to claim 16, wherein said attachment points are formed in said soft polymer.

* * * * *